(12) United States Patent
Zaima (10) Patent No.: US 12,232,747 B2
(45) Date of Patent: Feb. 25, 2025

(54) SURGICAL INSTRUMENT AND SURGICAL INSTRUMENT SYSTEM

(71) Applicant: KYOCERA Corporation, Kyoto (JP)

(72) Inventor: Hironori Zaima, Toyonaka (JP)

(73) Assignee: KYOCERA Corporation, Kyoto (JP)

( * ) Notice: Subject to any disclaimer, the term of this patent is extended or adjusted under 35 U.S.C. 154(b) by 505 days.

(21) Appl. No.: 17/413,864

(22) PCT Filed: Dec. 24, 2019

(86) PCT No.: PCT/JP2019/050699
§ 371 (c)(1),
(2) Date: Jun. 14, 2021

(87) PCT Pub. No.: WO2020/138114
PCT Pub. Date: Jul. 2, 2020

(65) Prior Publication Data
US 2022/0054145 A1    Feb. 24, 2022

(30) Foreign Application Priority Data
Dec. 25, 2018   (JP) .................. 2018-240743

(51) Int. Cl.
*A61B 17/15*   (2006.01)
*A61B 17/16*   (2006.01)
*A61B 17/17*   (2006.01)

(52) U.S. Cl.
CPC .......... *A61B 17/155* (2013.01); *A61B 17/151* (2013.01); *A61B 17/152* (2013.01); *A61B 17/154* (2013.01);
(Continued)

(58) Field of Classification Search
CPC ..... A61B 17/15; A61B 17/155; A61B 17/151; A61B 17/152; A61B 17/154;
(Continued)

(56) References Cited

U.S. PATENT DOCUMENTS 7,601,154 B2 * 10/2009 Kuczynski ........... A61B 17/157
606/88
2002/0133164 A1 * 9/2002 Williamson ......... A61B 17/025
606/90
(Continued)

FOREIGN PATENT DOCUMENTS

EP   0709061 A1   5/1996
FR   2726178 A1   5/1996
(Continued)

OTHER PUBLICATIONS

Triathlon PKR, Partial Knee Resurfacing Surgical Protocol, Stryker, Mahwah, NJ 07430, 2016, 36 pages.

*Primary Examiner* — Marcela I. Shirsat
(74) *Attorney, Agent, or Firm* — Procopio, Cory, Hargreaves & Savitch LLP (57) ABSTRACT

Provided are a surgical instrument and a surgical instrument system which has a simple structure and with which an osteotomy can be done with a simple operation. A surgical instrument includes a spacer part having a predetermined thickness, a guide part extending in a direction perpendicular to the guide part. The spacer part includes a first surface that abuts on one of posterior condyles of a femur at a bent position of a knee joint. The guide part includes a second surface that extends perpendicular to the first surface and abuts on a distal end part of the femur, and a guide slit penetrating the guide part along a direction parallel to the first surface and through which an osteotomy instrument is inserted.

6 Claims, 5 Drawing Sheets

(52) U.S. Cl.
CPC ......... *A61B 17/1675* (2013.01); *A61B 17/175* (2013.01); *A61B 17/1764* (2013.01)

(58) Field of Classification Search
CPC . A61B 17/1675; A61B 17/1662; A61B 17/17; A61B 17/1739; A61B 17/1764; A61B 17/175
USPC ................ 606/53, 79, 86 R, 87, 88, 89, 96; 623/13.12
See application file for complete search history.

(56) References Cited

U.S. PATENT DOCUMENTS

| | | | | |
|---|---|---|---|---|
| 2003/0100907 | A1* | 5/2003 | Rosa | A61B 17/1675 606/86 R |
| 2003/0225413 | A1* | 12/2003 | Sanford | A61B 17/155 606/87 |
| 2004/0153087 | A1* | 8/2004 | Sanford | A61F 2/4684 606/88 |
| 2005/0192588 | A1 | 9/2005 | Garcia | |
| 2006/0217734 | A1* | 9/2006 | Sanford | A61B 17/155 606/88 |
| 2006/0241639 | A1 | 10/2006 | Kuczynski et al. | |
| 2014/0058398 | A1 | 2/2014 | Kaneyama et al. | |
| 2015/0133943 | A1* | 5/2015 | Axelson, Jr. | A61B 17/155 606/89 |
| 2017/0007273 | A1* | 1/2017 | Freiberg | A61B 17/1764 |

FOREIGN PATENT DOCUMENTS

| | | |
|---|---|---|
| JP | 2012-170756 A | 9/2012 |
| JP | 2018-519926 A | 7/2018 |

\* cited by examiner

SURGICAL INSTRUMENT AND SURGICAL INSTRUMENT SYSTEM

CROSS-REFERENCE TO RELATED APPLICATION

This application is a national stage entry according to 35 U.S.C. 371 of International Application No. PCT/JP2019/050699 filed on Dec. 24, 2019, which claims priority to Japanese Patent Application No. 2018-240743 filed on Dec. 25, 2018, the contents of which are entirely incorporated herein by reference.

TECHNICAL FIELD

The present disclosure relates to a surgical instrument and a surgical instrument system used in total knee arthroplasty, and particularly used in unicompartmental knee arthroplasty.

BACKGROUND

In unicompartmental knee arthroplasty of a related art, in order to allow a knee to be smoothly bent and stretched after an artificial knee joint (hereinafter also referred to as an implant) is mounted, an osteotomy is performed by adjusting an amount of the osteotomy at a distal end of a femur in a stretched position state based upon a gap between a tibia and a posterior condyle of the femur at a bent position of the knee joint. With respect to the amount of the osteotomy at the distal end of the femur, a dimension of a stretched position gap, which is a distance between the tibia and the femur at a stretched position in a state where the implant is mounted, is adjusted to be equal to a dimension of a bent position gap, which is a distance between the tibia and the femur at a bent position in the state where the implant is mounted.

For example, an osteotomy procedure in the unicompartmental knee arthroplasty is performed by using a surgical instrument including a spacer part to be inserted between the femur and the tibia after a proximal end part of the tibia is resected, and a guide part to be mounted on the spacer part for guiding an osteotomy instrument that performs the osteotomy on the femur. Specifically, the osteotomy procedure is performed as follows.

First, a surgeon resects the proximal end part of the tibia facing a condyle (usually an inner condyle) on an affected side in a flat shape.

Next, the surgeon inserts the spacer part of the surgical instrument between the tibia whose proximal end part is resected and the femur. At this time, a spacer part having a maximum thickness that can be inserted between the proximal end part of the tibia and the distal end part of the femur in the respective states of the stretched position and the bent position. The thickness of the spacer part is confirmed and compared in the respective states of the stretched position and the bent position.

Next, in the stretched position state, the surgeon inserts the spacer part between the proximal end part of the tibia and the distal end part of the femur, and mounts a first guide part including a slit for resecting the distal end of the femur on the spacer part. Next, the distal end of the femur is resected with the osteotomy instrument guided by the slit of the first guide part. A position at which the distal end of the femur is resected at this time is set so that the dimension of the stretched position gap after the implant is mounted is equal to the dimension of the bent position gap before the osteotomy is performed.

Next, the surgeon removes the first guide part from the spacer part, and puts the patient's knee joint in the stretched position state into the bent position state. Next, after a second guide part including a slit for resecting and chamfering the posterior condyle of the femur is mounted on the spacer part, the guide part is fixed to the distal end part of the osteotomized femur with a pin.

After fixing the guide part thereto, the surgeon removes the spacer part and resects the posterior condyle of the femur by a thickness of the implant, with the osteotomy instrument. Next, the surgeon chamfers the distal end part of the femur from which the posterior condyle of the femur is resected, with the osteotomy instrument. Next, the implant is mounted on the distal end part of the femur that is osteotomized by the above-described procedures. An object of the above-described procedures is that a resection position of the distal end of the femur is adjusted and then the osteotomy is performed to allow the stretched position gap and the bent position gap to have the same dimension, such that bending and stretching of the knee joint after the implant is mounted is smoothly performed.

SUMMARY

A surgical instrument according to the disclosure is a surgical instrument for guiding an osteotomy instrument that resects one of posterior condyles of a femur, the surgical instrument including: a spacer part including a first surface that abuts on one of the posterior condyles of the femur and having a predetermined thickness; a guide part including a second surface that intersects the first surface of the spacer part and abuts on a distal end part of the femur, the guide part being connected to the spacer part; and a guide slit through which the osteotomy instrument can be inserted, the guide slit penetrating the guide part along a direction parallel to the first surface.

A surgical instrument system according to the disclosure includes at least two surgical instruments for guiding an osteotomy instrument that resects one of posterior condyles of a femur. The at least two surgical instruments each include: a spacer part including a first surface that abuts on one of the posterior condyles of the femur and having a predetermined thickness; a guide part including a second surface that intersects the first surface of the spacer part and abuts on a distal end part of the femur, the guide part being connected to the spacer part; and a guide slit through which the osteotomy instrument can be inserted, the guide slit penetrating the guide part along a direction parallel to the first surface. The at least two surgical instruments have different distances from the first surfaces to the guide slits, respectively.

BRIEF DESCRIPTION OF DRAWINGS

Other and further objects, features, and advantages of the disclosure invention will be more explicit from the following detailed description taken with reference to the drawings wherein.

DETAILED DESCRIPTION

Hereinafter, embodiments of the disclosure will be described with reference to the drawings. The disclosure can be widely applied as a surgical instrument and a surgical instrument system used in unicompartmental knee arthroplasty.

In the unicompartmental knee arthroplasty of a related art, for example, a plurality of components are required during surgery, such as using a first guide part and a second guide part that are separate from a spacer part. In order to allow bending and stretching of a knee joint to be smoothly performed, an amount of an osteotomy is adjusted in a stretched position state to resect a distal end of a femur, but a posterior condyle of the femur is not resected by adjusting the amount of the osteotomy in a bent position state. Therefore, it is desired to achieve an instrument in which a gap can be easily adjusted with a simple operation by resecting the posterior condyle of the femur in the bent position state so that a dimension of a stretched position gap and a dimension of a bent position gap after an implant is mounted are the same as each other.

Figure 1:
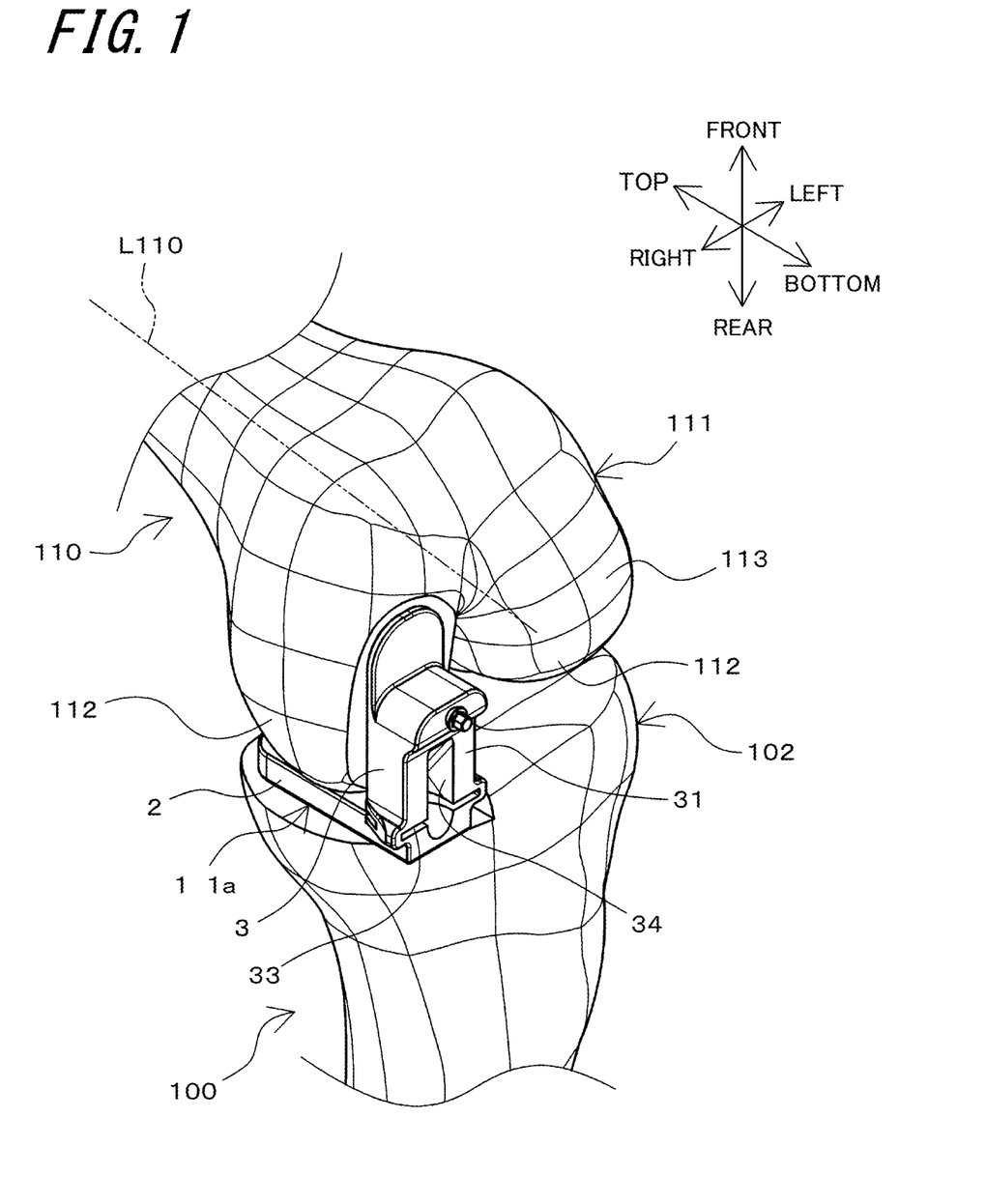
FIG. 1 is a diagram illustrating a surgical instrument according to one embodiment of the disclosure, and is a diagram illustrating a state where the surgical instrument is mounted on a distal end part of a femur.
Figure 2:
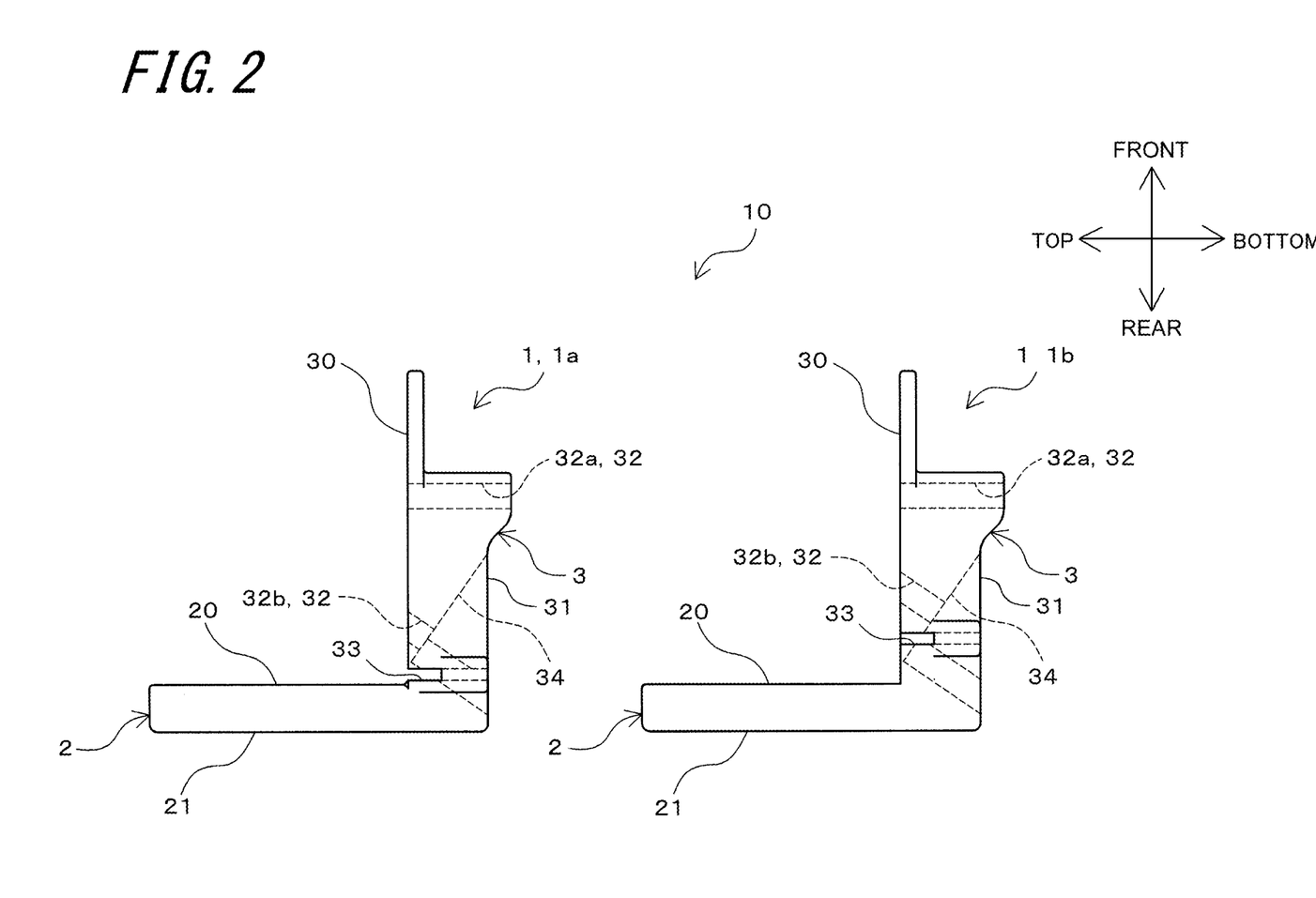
FIG. 2 is a diagram illustrating a surgical instrument system according to one embodiment of the disclosure.
Figure 3:
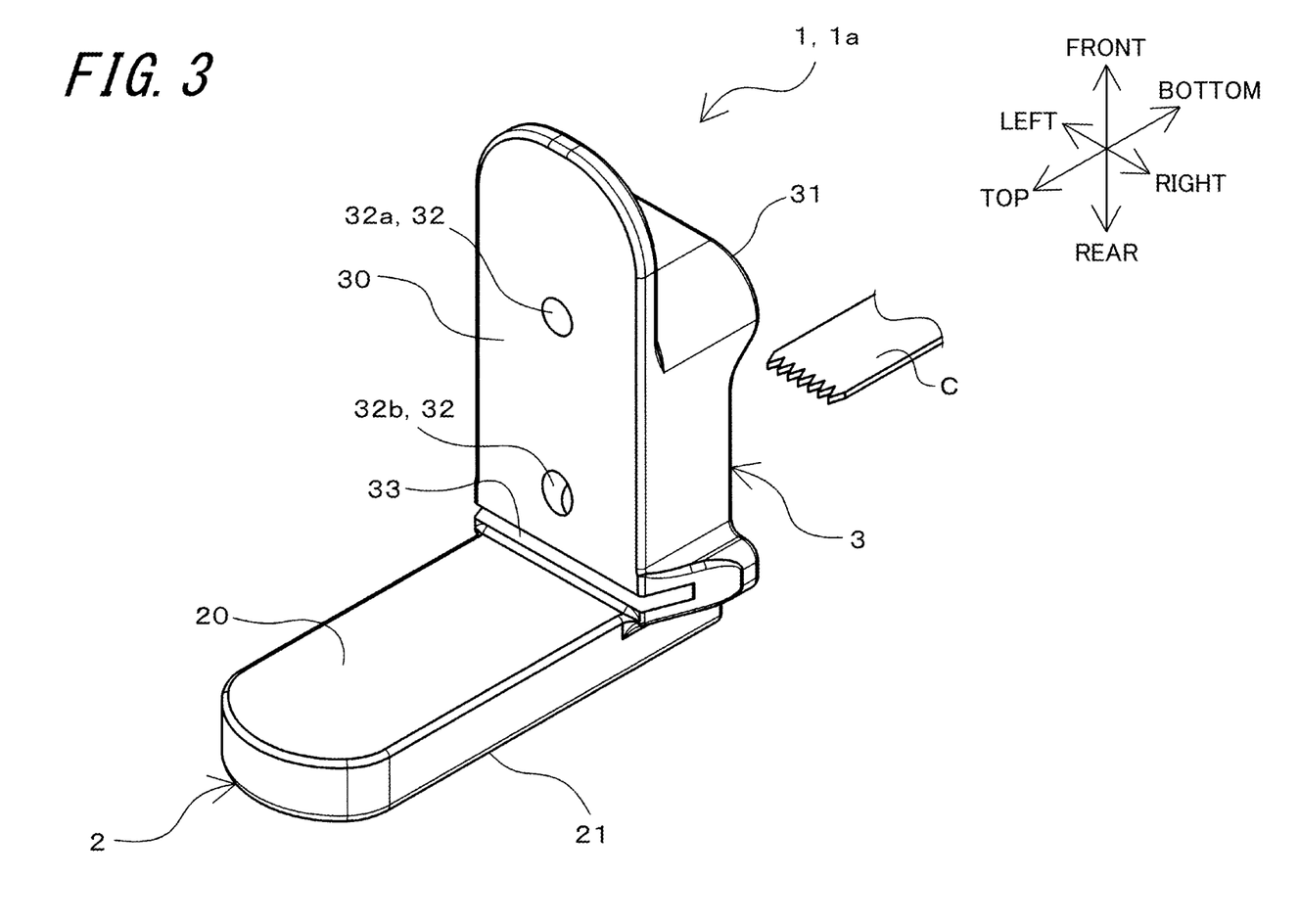
FIG. 3 is a perspective view illustrating the surgical instrument according to one embodiment of the disclosure.
Figure 4:
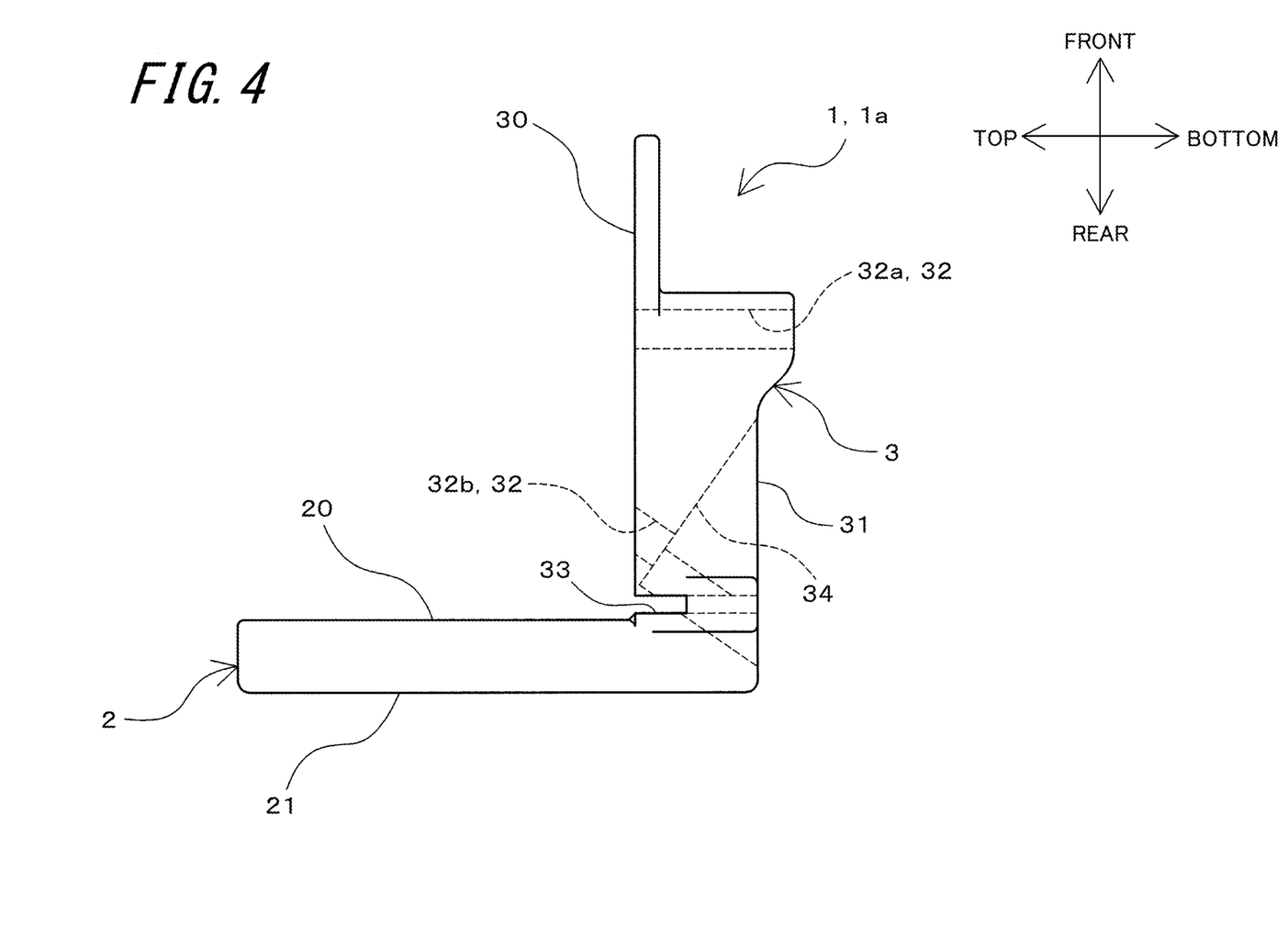
FIG. 4 is a side view illustrating the surgical instrument illustrated in FIG. 3.
Figure 5:
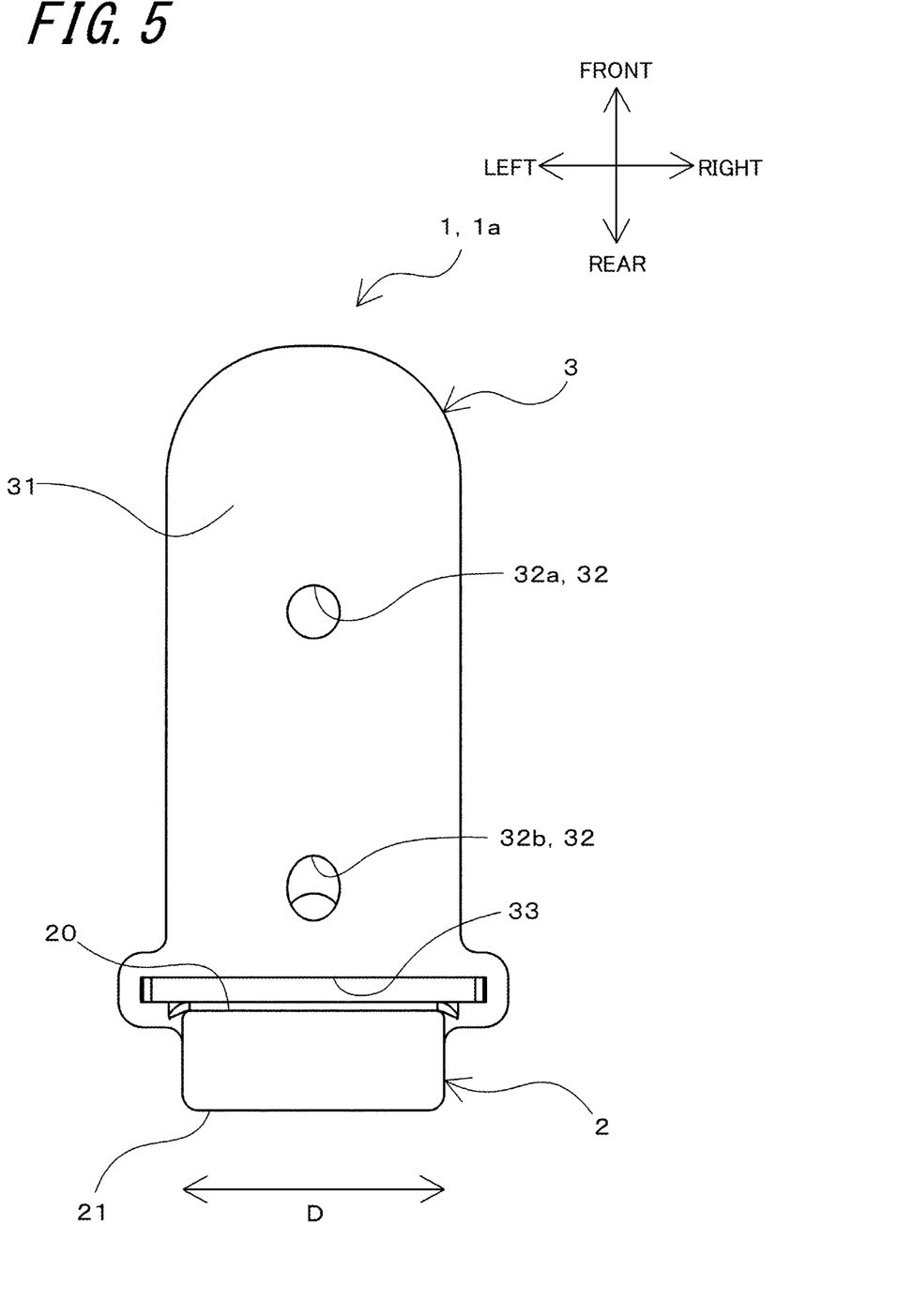
FIG. 5 is a front view illustrating the surgical instrument illustrated in FIG. 3.

FIG. 1 is a diagram illustrating a surgical instrument according to one embodiment of the disclosure, and is a diagram illustrating a state where a surgical instrument 1 is mounted on a distal end part 111 of a femur. FIG. 1 illustrates an example of a state where the surgical instrument 1 is mounted on a medial condyle side of a left leg knee joint of a human body. FIG. 2 is a diagram illustrating a surgical instrument system 10 according to one embodiment of the disclosure. FIG. 3 is a perspective view illustrating the surgical instrument 1 according to one embodiment of the disclosure. FIG. 4 is a side view illustrating the surgical instrument 1 illustrated in FIG. 3. FIG. 5 is a front view illustrating the surgical instrument 1 illustrated in FIG. 3. In FIGS. 1 and 3, thin lines are attached to represent an outer shape.

Directions illustrated in each drawing are described with reference to the human body when the surgical instrument is mounted in the bent position state. Specifically, in each drawing, directions, respectively, described as front, rear, top, bottom, left, and right correspond to directions of front, rear, top, bottom, left, and right of the human body. A direction indicated by an arrow described as "top" is referred to as a top side or upward, a direction indicated by an arrow described as "bottom" is referred to as a bottom side or downward, a direction indicated by an arrow described as "front" is referred to as a front side or forward, a direction indicated by an arrow described as "rear" is referred to as a rear side or rearward, a direction indicated by an arrow described as "left" is referred to as a left side or leftward, and a direction indicated by an arrow described as "right" is referred to as a right side or rightward. A left and right direction is also referred to as a width direction D.

In the unicompartmental knee arthroplasty, the surgical instrument 1 illustrated in the embodiment is used for guiding a long thin plate-shaped osteotomy instrument C for resecting one of posterior condyles 112 of a femur 110. A plurality of surgical instruments 1 used in the unicompartmental knee arthroplasty in the embodiment are used as the surgical instrument system 10. That is, when the posterior condyle 112 of the femur is resected, for example, as illustrated in FIG. 2, the surgical instrument system 10 uses at least two surgical instruments 1a and 1b. Each of the surgical instruments 1a and 1b of the surgical instrument system 10 has a different position at which a guide slit 33, which will be described later, is provided.

Referring to FIG. 1, the surgical instrument 1 is arranged and used between a tibia 100 and the femur 110 in the unicompartmental knee arthroplasty. More specifically, the surgical instrument 1 is mounted in a state of facing the distal end part 111 of the femur and one side of the posterior condyle 112 of the femur resected by the osteotomy instrument C such as a bone saw. The surgical instrument 1 includes a spacer part 2 and a guide part 3. The surgical instrument system 10 is used for resecting the posterior condyle 112 of the femur at a predetermined position, and includes a plurality of surgical instruments 1. The surgical instrument system 10 used in the unicompartmental knee arthroplasty according to the embodiment is formed of two surgical instruments 1 including the surgical instrument 1a and the surgical instrument 1b. The surgical instrument 1a and the surgical instrument 1b have different distances from posterior condyle contact surfaces 20 (also referred to as first surfaces) which will be described later to guide slits 33, respectively.

The spacer part 2 is arranged at a position facing the posterior condyle 112 of the femur 110. The spacer part 2 is provided as a member that has a predetermined thickness and extends in a flat plate shape. The spacer part 2 has a certain width between a proximal end part 101 of the tibia and the posterior condyle 112 of the femur and extends in a front and rear direction when the knee joint is in the bent position state. The spacer part 2 is provided along the posterior condyle 112 of the femur 110. Referring to FIG. 2, the spacer part 2 includes the posterior condyle contact surface 20 (also referred to as the first surface) and a tibia facing surface 21.

Referring to FIGS. 1 to 4, the posterior condyle contact surface 20 is formed in a flat shape as a surface of the spacer part 2 on a side facing the posterior condyle 112 of the femur 110. The posterior condyle contact surface 20 abuts on one of the posterior condyles 112 of the femur 110 when a patient's knee joint is in the bent position state. More specifically, the posterior condyle contact surface 20 of the spacer part 2 abuts on the most protruding portion of the posterior condyle 112 of the femur 110. The tibia facing surface 21 is formed in a flat shape as a surface of the spacer part 2 on a side facing the tibia 100.

The guide part 3 is arranged at a position facing a distal end 113 of the femur 110. The guide part 3 has a predetermined thickness and is provided as a portion arranged along the distal end 113 of the femur 110. The guide part 3 extends forward from a lower end of the spacer part 2. That is, the guide part 3 extends in the front and rear direction which is a direction perpendicular to the spacer part 2. The guide part 3 includes a distal end part contact surface 30 (also referred to as a second surface), an outer surface 31, a pin hole 32, the guide slit 33, and a recessed part 34.

The distal end part contact surface 30 is formed in a flat shape as a surface of the guide part 3 on a side facing the distal end 113 of the femur 110. The distal end part contact surface 30 is provided so as to intersect the posterior condyle contact surface 20 of the spacer part 2, and more specifically, extends in a direction perpendicular to the posterior condyle contact surface 20. The distal end part contact surface 30 abuts on the distal end 113 of the femur 110. More specifically, the distal end part contact surface 30 of the guide part 3 abuts on a surface of the resected distal end 113 of the femur. When the surgical instrument 1 is mounted without resecting the distal end 113 of the femur, the distal end part contact surface 30 abuts on the most protruding portion of the distal end 113 of the femur 110. The outer surface 31 is configured as a surface on a side into which a pin, which is not illustrated, is inserted.

The pin hole 32 is provided as a through hole that penetrates the guide part 3. A pin for fixing the surgical instrument 1 to the femur 110 is inserted through the pin hole 32. The pin hole 32 holds the distal end part contact surface 30 at the distal end 113 of the femur 110 by allowing the pin inserted into the femur 110 to be inserted therethrough. At least two pin holes 32 are provided in the guide part 3. The at least two pin holes 32 provided in the guide part 3 penetrate the guide part 3 in different directions.

As illustrated in FIGS. 2 to 5, the two pin holes 32 according to the embodiment are provided in the guide part 3, and a pin hole 32a is provided to penetrate through the guide part 3 in a vertical direction, that is, in a direction parallel to an axis L110 of the femur 110 illustrated in FIG. 1. As illustrated in FIG. 4, a pin hole 32b is provided to penetrate through the guide part 3 so as to approach the pin hole 32a as the pin hole 32b moves from the outer surface 31 toward the distal end part contact surface 30. As a result, the surgical instrument 1 can be more firmly fixed by a plurality of pins so as not to move with respect to the femur, and an osteotomy operation can be performed more easily in a stable state. In comparison with a surgical instrument in which a plurality of pin holes that penetrate the guide part 3 in the same direction are provided, it is possible to restrain the surgical instrument 1 from easily coming off in a direction in which the pin is pulled out and pierced while allowing the surgical instrument 1 to be easily mounted on the bone.

The guide slit 33 is provided for performing the osteotomy on the posterior condyle 112 of the femur at a predetermined position by inserting the osteotomy instrument C. The guide slit 33 penetrates the guide part 3 along a direction parallel to the posterior condyle contact surface 20 at a position separated forward from the posterior condyle contact surface 20 of the spacer part 2 by a predetermined distance. As illustrated in FIG. 3, the osteotomy instrument C is inserted into the guide slit 33 from a side of the outer surface 31. The osteotomy instrument C inserted into the guide slit 33 can resect the posterior condyle 112 of the femur so as to form a resected surface parallel to the posterior condyle contact surface 20 at the position separated from the posterior condyle contact surface 20 of the spacer part 2 by the predetermined distance.

Referring to FIG. 5, a portion of the guide part 3 where the guide slit 33 is provided is configured to have a larger dimension in the width direction D than that of a portion of the guide part 3 where the guide slit 33 is not provided. The guide slit 33 is configured to have a width larger than a width of the guide part 3. The guide slit 33 is formed in a state where a side of the distal end part contact surface 30 of the guide part 3 is opened outward on both side surfaces which are surfaces in the left and right direction of the guide part 3. Therefore, the osteotomy instrument C inserted into the guide slit 33 can be operated to widely shake a tip side of a blade in the width direction of the surgical instrument 1, that is, in the left and right direction, such that the entire surgical instrument can be formed to be compact while ensuring a movable range.

As illustrated in FIGS. 1, 2, and 4, the recessed part 34 is formed on the side of the outer surface 31 of the guide part 3. The pin hole 32b is arranged in the recessed part 34 so that the pin to be inserted into the pin hole 32b does not interfere with the bone saw to be inserted into the guide slit 33.

The at least two surgical instruments 1a and 1b used in the unicompartmental knee arthroplasty according to the embodiment are configured so that distances along the front and rear direction from the posterior condyle contact surface 20 of the spacer part 2 to the guide slit 33 are different from each other. Specifically, as illustrated in FIG. 2, when surgery is performed, the two surgical instruments 1 including the guide slits 33 having different positions at which the posterior condyle 112 of the femur is resected are provided, thereby being replaced depending on a thickness of the posterior condyle 112 of the femur to be osteotomized.

A procedure for the osteotomy of the embodiment is performed by using the above-described surgical instrument 1. Hereinafter, the procedure for the osteotomy to be performed by using the surgical instrument 1 will be described.

In the osteotomy of the embodiment, first, an osteophyte at the distal end part 111 of the femur is removed in the bent position state. Next, a portion of the proximal end part 101 of the tibia facing one side of the posterior condyle 112 of the femur is resected to be formed in a flat shape by using a dedicated instrument which is not illustrated.

Next, the surgical instrument 1 in which the spacer part 2 and the guide part 3 are formed to be integrated with each other is installed on the femur 110 so that the spacer part 2 is inserted between the tibia 100 whose proximal end part is resected and the femur 110. At this time, in order to adjust the amount of the osteotomy of the posterior condyle contact surface 20 after confirming a stretched position gap and a bent position gap, the surgical instrument 1 having an appropriate distance from the posterior condyle contact surface 20 to the guide slit 33 is installed in the knee joint. When the surgical instrument 1 is installed on the knee joint, the distal end part 111 of the femur may be resected in a flat shape in advance.

The surgical instrument 1 installed on the knee joint is fixed to the distal end part 111 of the femur with the pin in a state where the posterior condyle contact surface 20 of the spacer part 2 abuts on the posterior condyle 112 of the femur, and the distal end part contact surface 30 of the guide part 3 is in contact with the distal end 113 of the femur.

After the surgical instrument 1 is fixed to the distal end part 111 of the femur, the posterior condyle 112 of the femur is resected with the osteotomy instrument C guided by the guide slit 33.

Next, the surgical instrument 1 is removed from the distal end part 111 of the femur, and the distal end part 111 of the femur is resected by a thickness of the implant. Further, after the distal end part 111 of the femur is chamfered, the implant is mounted. The bent position gap and the stretched position gap after the implant is mounted become the same dimension by the unicompartmental knee arthroplasty performed by the above-described procedures, such that the patient can smoothly bend and stretch the knee joint.

[Action and Effect of the Embodiment]

The surgical instrument 1 and the surgical instrument 1 of the surgical instrument system 10 according to the embodiment include the spacer part 2 and the guide part 3 that extends in the direction perpendicular to the spacer part 2. Therefore, the surgeon can arrange the spacer part 2 of the surgical instrument 1 along the posterior condyle 112 of the femur and can also arrange the guide part 3 thereof along the distal end part 111 of the femur. The spacer part 2 includes the posterior condyle contact surface 20 that abuts on one of the posterior condyles 112 of the femur in the bent position state, and the guide part 3 includes: the distal end part contact surface 30 that extends perpendicular to the posterior condyle contact surface 20 and abuts on the distal end part 111 of the femur; the pin hole 32 for holding the distal end part contact surface 30 at the distal end part 111 of the femur; and the guide slit 33 into which the osteotomy instrument C is inserted. Therefore, in the unicompartmental knee arthroplasty, the surgeon can excise the posterior condyle 112 of the femur at the bent position with the osteotomy instrument C guided by the guide slit 33 by using the surgical instrument 1 having a simple structure as described above.

In a related art, in order to achieve the smooth bending of the knee joint, in the unicompartmental knee arthroplasty, the distal end part 111 of the femur has been resected in the stretched position state so that the dimension of the bent position gap and the dimension of the stretched position gap after the implant is mounted are the same as each other. Therefore, it has taken time and has required an effort to adjust the gap at the stretched position. However, according to the surgical instrument 1 and the surgical instrument 1 of the surgical instrument system 10, it is possible to perform the osteotomy by adjusting the amount of the osteotomy of the posterior condyle 112 of the femur at the bent position. Accordingly, when the posterior condyle 112 of the femur is resected by the osteotomy instrument C guided by the guide slit 33 of the guide part 3, adjustment can be performed so that the dimension of the bent position gap after the implant is mounted is the same as the dimension of the stretched position gap before the osteotomy is performed. Therefore, it is not necessary to adjust the amount of the osteotomy of the distal end 113 of the femur in the stretched position state so that the stretched position gap and the bent position gap after the implant is mounted have the same dimension. As a result, in the unicompartmental knee arthroplasty, the amount of the osteotomy of the posterior condyle 112 of the femur is adjusted at the bent position, such that the osteotomy can be performed with a simple operation of performing resection by the thickness of the implant without adjusting the amount of the osteotomy at the stretched position.

Therefore, it is possible to provide the surgical instrument 1 and the surgical instrument 1 of the surgical instrument system 10 having a simple structure and capable of performing the osteotomy with a simple operation.

According to the above-described configuration, the surgical instrument 1 of the surgical instrument system 10 includes the guide part 3 including the guide slit 33 that penetrates the guide part 3 along the direction parallel to the posterior condyle contact surface 20 and into which the osteotomy instrument C is inserted. At least two or more surgical instruments 1 of the surgical instrument system 10 are provided, and the distances thereof from the posterior condyle contact surface 20 to the guide slit 33 are respectively different from each other. Therefore, when the posterior condyle 112 of the femur is resected at the bent position, the amount of the osteotomy can be simply adjusted by replacing the surgical instrument 1.

According to the surgical instrument 1, the guide part 3 includes at least two pin holes 32 as through holes. The pins for fixing the surgical instrument 1 to the femur 110 are inserted into these at least two pin holes 32. Accordingly, the surgical instrument 1 is more firmly fixed thereto by the plurality of pins so as not to move with respect to the femur.

According to the surgical instrument 1, the at least two pin holes 32 provided in the guide part 3 penetrate the guide part 3 in different directions. Therefore, in comparison with the guide part 3 including a plurality of pin holes 32 that penetrate the guide part 3 in the same direction, it is possible to restrain the surgical instrument 1 from easily coming off in a direction in which the pin is pulled out and pierced while allowing the surgical instrument 1 to be easily mounted on the bone.

According to the surgical Instrument 1, as illustrated in FIG. 5, the dimension in the width direction D of the portion of the guide part 3 where the guide slit 33 is provided is formed to be larger than that of the portion of the guide part 3 where the guide slit 33 is not provided. Accordingly, the entire surgical instrument can be formed to be compact while ensuring the movable range of the osteotomy instrument that resects the bone in a state of being inserted into the guide slit.

MODIFICATIONS

While the embodiment of the disclosure is described above, the disclosure is not limited to the above-described embodiment, and modifications can be made and performed in various ways as long as the modifications are within the scope of the claims. For example, the following modifications may be performed.

(1) The above-described embodiment describes a case as an example in which two surgical instruments 1a and 1b are provided and used as the surgical instrument system 10 used in the unicompartmental knee arthroplasty, but the disclosure may not be limited to the case. For example, one surgical instrument 1 may be provided and used for surgery, or three or more surgical instruments 1 may be provided and used for the surgery.

(2) The above-described embodiment describes the surgical instrument 1 in which the spacer part 2 and the guide part 3 are formed to be integrated with each other as an example, but the disclosure may not be limited thereto. For example, the spacer part 2 and the guide part 3 may be formed as separate bodies and may be used in combination during the surgery.

The disclosure may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

INDUSTRIAL APPLICABILITY

The disclosure is widely applicable as a surgical instrument and a surgical instrument system used in unicompartmental knee arthroplasty.

REFERENCE SIGNS LIST

1: Surgical instrument
10: Surgical instrument system
2: Spacer part
20: Posterior condyle contact surface (First surface)
3: Guide part
30: Distal end part contact surface (Second surface)
32: Pin hole
33: Guide slit
100: Tibia
110: Femur
111: Distal end part of femur
112: Posterior condyle 112 of femur
C: Osteotomy instrument
D: Width direction

The invention claimed is:

1. A surgical instrument for guiding an osteotomy instrument that resects one of posterior condyles of a femur, the surgical instrument comprising:
    a spacer part comprising a first surface configured to abut on one of posterior condyles of a femur and having a predetermined thickness;
    a guide part comprising a second surface that intersects the first surface of the spacer part and configured to abut on a distal end part of the femur, the guide part being connected to the spacer part; and
    a guide slit through which an osteotomy instrument can be inserted, the guide slit penetrating the guide part along a direction parallel to the first surface, and comprising a first closed portion located on a left side of the guide slit and a second closed portion located on a right side of the guide slit, the guide slit including an entrance opening having a width and an exit opening including a width greater than the width of the entrance opening,
    wherein the guide slit is open from the second surface to both right and left sides of the guide part.

2. The surgical instrument according to claim 1, wherein the guide part further comprises pin holes that are each configured to receive a pin that is configured to be inserted into the femur, and
    each of the pin holes is provided as a through hole penetrating the guide part, and at least two pin holes are provided in the guide part.

3. The surgical instrument according to claim 2, wherein the at least two pin holes provided in the guide part penetrate the guide part in different directions.

4. The surgical instrument according to claim 1, wherein a portion of the guide part where the guide slit is provided has a larger dimension in a width direction than that of a portion of the guide part where the guide slit is not provided.

5. The surgical instrument according to claim 1, further comprising
    a recessed part being open on an opposite surface of the second surface, and
    a pin hole extending from an inner surface of the recessed part to the second surface.

6. A surgical instrument system comprising:
    at least two surgical instruments for guiding an osteotomy instrument that resects one of posterior condyles of a femur,
    the at least two surgical instruments each comprising
    a spacer part comprising a first surface configured to abut on one of the posterior condyles of the femur and having a predetermined thickness;
    a guide part comprising a second surface that intersects the first surface of the spacer part and configured to abut on a distal end part of the femur, the guide part being connected to the spacer part; and
    a guide slit through which the osteotomy instrument can be inserted, the guide slit penetrating the guide part along a direction parallel to the first surface, and comprising a first closed portion located on a left side of the guide slit and a second closed portion located on a right side of the guide slit, the guide slit including an entrance opening having a width and an exit opening including a width greater than the width of the entrance opening, and
    the at least two surgical instruments having different distances from the first surfaces to the guide slits,
    wherein the guide slit is open from the second surface to both right and left sides of the guide part.

* * * * *